(12) United States Patent
Brown (10) Patent No.: US 10,768,402 B2
(45) Date of Patent: Sep. 8, 2020

(54) MICROSCOPY OF A TISSUE SAMPLE USING STRUCTURED ILLUMINATION

(71) Applicant: The Administrators of the Tulane Educational Fund, New Orleans, LA (US)

(72) Inventor: Jonathon Quincy Brown, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 0 days.

(21) Appl. No.: 16/054,235

(22) Filed: Aug. 3, 2018

(65) Prior Publication Data

US 2018/0348496 A1 Dec. 6, 2018

Related U.S. Application Data

(63) Continuation of application No. 14/888,257, filed as application No. PCT/US2014/038141 on May 15, 2014, now Pat. No. 10,042,150.

(Continued)

(51) Int. Cl.
*G02B 21/16* (2006.01)
*G02B 21/00* (2006.01)
(Continued)

(52) U.S. Cl.
CPC ............ *G02B 21/16* (2013.01); *A61B 5/0071* (2013.01); *A61B 10/02* (2013.01); *G01N 1/30* (2013.01);
(Continued)

(58) Field of Classification Search
None
See application file for complete search history.

(56) References Cited

U.S. PATENT DOCUMENTS 6,671,540 B1 12/2003 Hochman
7,139,598 B2 11/2006 Hull et al.
(Continued)

FOREIGN PATENT DOCUMENTS

EP 2110697 A1 10/2009
JP 20000095758 A 3/2000
(Continued)

OTHER PUBLICATIONS

Huisken et al., "Even Fluorescence Excitation by Multidirectional Selective Plane Illumination Microscopy," Opt. Lett. 32 (17), 2608-2610, 2007. (Year: 2007).*

(Continued)

*Primary Examiner* — Christopher Braniff
(74) *Attorney, Agent, or Firm* — Tarolli, Sundheim, Covell & Tummino LLP (57) ABSTRACT

Systems and methods are provided for evaluating a fresh tissue sample, prepared as to fluoresce under illumination, during a medical procedure. A structured light source is configured to project a spatially patterned light beam onto the fresh tissue sample. An imaging system is configured to produce an image from fluorescence emitted from the illuminated fresh tissue sample. A system control is configured to provide a human-comprehensible clinically useful output associated with the medical procedure.

15 Claims, 4 Drawing Sheets

Related U.S. Application Data (60) Provisional application No. 61/919,434, filed on Dec. 20, 2013, provisional application No. 61/823,817, filed on May 15, 2013.

(51) Int. Cl.
  *H04N 5/225* (2006.01)
  *G01N 21/64* (2006.01)
  *A61B 5/00* (2006.01)
  *A61B 10/02* (2006.01)
  *G01N 1/30* (2006.01)
  *G02B 21/36* (2006.01)
  *G06K 9/52* (2006.01)
  *G06K 9/62* (2006.01)
  *A61B 90/00* (2016.01)

(52) U.S. Cl.
  CPC ..... *G01N 21/6458* (2013.01); *G02B 21/0076* (2013.01); *G02B 21/365* (2013.01); *G02B 21/367* (2013.01); *G06K 9/52* (2013.01); *G06K 9/6267* (2013.01); *H04N 5/2256* (2013.01); *A61B 2090/366* (2016.02); *A61B 2090/3941* (2016.02); *G01N 2001/302* (2013.01); *G01N 2021/6419* (2013.01); *G01N 2021/6421* (2013.01); *G01N 2021/6441* (2013.01); *G01N 2201/0635* (2013.01); *G01N 2201/0675* (2013.01); *G01N 2201/129* (2013.01)

(56) References Cited

U.S. PATENT DOCUMENTS

| | | | |
|---|---|---|---|
| 8,406,859 B2 | 3/2013 | Zuzak et al. | |
| 8,504,140 B2 | 8/2013 | Feke et al. | |
| 2005/0094147 A1* | 5/2005 | Yaroslavsky | A61B 5/0059 356/417 |
| 2006/0118742 A1* | 6/2006 | Levenson | A61B 5/0059 250/559.3 |
| 2008/0103390 A1 | 5/2008 | Contag et al. | |
| 2009/0250631 A1 | 10/2009 | Feke et al. | |
| 2010/0056928 A1 | 3/2010 | Zuzak et al. | |
| 2011/0182529 A1 | 7/2011 | Kempe | |
| 2011/0194175 A1 | 8/2011 | Dougherty | |
| 2011/0224574 A1 | 9/2011 | Sadler et al. | |
| 2012/0108982 A1 | 5/2012 | Hoyt | |
| 2012/0307247 A1 | 12/2012 | Tan et al. | |
| 2013/0044185 A1 | 2/2013 | Krishnaswamy et al. | |

FOREIGN PATENT DOCUMENTS

| | | |
|---|---|---|
| JP | 2007199572 A | 1/2006 |
| JP | 2010151566 A | 12/2008 |
| JP | 2012163795 A | 2/2011 |
| JP | 2012504252 A | 2/2012 |
| JP | 20130024792 A | 2/2013 |
| JP | 20130088808 A | 4/2013 |
| WO | 2010/132990 A1 | 11/2010 |
| WO | 2012/049831 A1 | 4/2012 |
| WO | 2012/135823 A1 | 10/2012 |
| WO | 2013/021615 A1 | 2/2013 |

OTHER PUBLICATIONS

Office Action for corresponding JP Patent Application No. 2016-514083, dated Dec. 20, 2016, pp. 1-3.
Extended European Report for corresponding EP Application No. 14797836.5 dated Nov. 28, 2016, pp. 1-15.
Fu, Henry L., et al. "Optimization of a widefield structured illumination microscope for non-destructive assessment and quantification of nuclear features in tumor margins of a primary mouse model of sarcoma." PloS one 8.7 (2013): e68868.
Schlichenmeyer, Tyler C., et al. "Video-rate structured illumination microscopy for high-throughput imaging of large tissue areas." Biomedical optics express 5.2 (2014): 366-377.
Fu, Henry L., et al. "Optimization of illumination frequency and preclinical validation of a wide-field structured illumination microscope designed for imaging in situ tumor margins." CLEO: Applications and Technology. Optical Society of America, 2013.
Australian Examination Report dated Jun. 6, 2016 for corresponding Int'l Pat. Appl. No. PCT/US2014/038141, pp. 1-3.
Canadian Examination Report dated Sep. 13, 2016 for corresponding Int'l Pat. Appl. No. PCT/US2014/038141, pp. 1-3.
PCT International Search Report for corresponding Int'l Patent Application No. PCT/US2014/038141, dated Sep. 25, 2014, pp. 1-3.
Japanese Office Action corresponding to Japanese Application Serial No. 2016-514083, dated Sep. 27, 2017, pp. 1-4.
Israel Office Action corresponding to Israel Application Serial No. 242474, dated Dec. 18, 2017, pp. 1-2.
Canadian Office Action corresponding to Canadian Application Serial No. 2912401, dated Jun. 27, 2017, pp. 1-4.
EP Examination Report dated Apr. 30, 2020 for corresponding EP Application No. 14797836.5.

* cited by examiner

MICROSCOPY OF A TISSUE SAMPLE USING STRUCTURED ILLUMINATION

RELATED APPLICATIONS

This application claims priority to U.S. Provisional Patent Application Ser. No. 61/823,817, filed May 15, 2013, and U.S. Provisional Patent Application Ser. No. 61/919,434, filed Dec. 20, 2013. The entire contents of both applications are hereby incorporated by reference, such that where an element or a part of the description, claims or drawings of this application is not otherwise contained in the text of the application but is completely contained in either or both of the '817 and the '434 applications, that element or part is hereby incorporated by reference for the purposes of Rule 20.6.

TECHNICAL FIELD

This invention relates to medical imaging systems, and more particularly, to microscopy of a tissue sample using structured illumination.

BACKGROUND

A number of clinical situations could be benefited by a more rapid histological processing method, which reduces the number of steps between obtaining a fresh tissue specimen and rendering a diagnosis. For example, there is a need for rapid pathologic detection of residual cancer on the surface of tumor resection specimens, known as positive tumor margins, such that the surgical procedure can be revised in time to prevent cancer from being left behind in the patient. Tumor excision is a very common treatment in solid cancers, where the surgeon must remove all of the diseased tissue from the patient to minimize the risk of cancer recurrence. Complete surgical removal offers the best prognosis for many types of cancer, especially those that have not metastasized. In most cases, the goal of these surgeries or tumor resections is to achieve cancer-free (or negative) surgical margins, thereby lowering the risk of local tumor recurrence. Surgical margin status has been shown to be a powerful predictor of local recurrence in several cancers including breast, brain, oral, head and neck, hepatic, esophageal, colorectal, prostate, and cervical cancers, as well as in soft-tissue sarcomas located in the extremities, trunk, and head and neck regions.

Currently, there are very few intra-operative tools available to assist surgeons in tumor margin diagnosis to ensure complete removal of the tumor. Touch prep cytology and frozen section analysis are two intra-operative tools currently implemented in some clinics, but both require a trained pathologist and other resources. Intraoperative pathology for surgical tumor resections is expensive and time-consuming and consequently is only available at a handful of surgery centers in the US. Thus, there is a clear unmet clinical need for effective intraoperative tools that can quickly examine the microscopic properties of surgical margins. Optical imaging techniques are particularly attractive for this application as entire margins can be intra-operatively imaged non-destructively and, potentially, in situ.

Fluorescence microscopy can be combined with a suitable bio-marker to generate additional nuclear-specific contrast, thereby allowing for the quantitation of nuclear size and density. In conventional fluorescence microscopy, the entire field of view is uniformly illuminated with the excitation light. This creates a problem as fluorophores outside the plane of focus are also excited and emit photons, generating a significant amount of unwanted background fluorescence. This in turn significantly degrades contrast of features of interest in the focal plane. This is a common issue in wide-field fluorescence microscopy and several specialized techniques exist to reject background fluorescence, such as fluorescence confocal microscopy. While effective in rejecting background fluorescence, confocal microscopy requires specialized optics in the form of rapid scanning mirrors and adjustable pinhole collection, which increases the cost and decreases the speed, which hinders the intra-operative intra-operative clinical feasibility. In addition, the amount of photons collected at each beam scan position is limited, so the system requires a sensitive detector, such as a photomultiplier tube. Further, because of the small field of view, the beam position has to be raster scanned to be able to survey an area that is in on the order of square millimeter to square centimeter.

SUMMARY OF THE INVENTION

In accordance with an aspect of the present invention, a system is provided for evaluating a fresh tissue sample, prepared as to fluoresce under illumination, during a medical procedure. A structured light source is configured to project a spatially patterned light beam onto the fresh tissue sample. An imaging system is configured to produce an image from fluorescence emitted from the illuminated fresh tissue sample. A system control is configured to provide a human-comprehensible clinically useful output associated with the medical procedure.

In accordance with another aspect of the present invention, a method is provided for rapidly evaluating a tissue sample removed during a medical procedure. The tissue sample is prepared such that the tissue will fluoresce under illumination. Spatially patterned illumination is projected onto the tissue sample. The fluorescence emitted from the sample is imaged during the medical procedure. A human-comprehensible, clinically useful output is provided.

In accordance with yet another aspect of the present invention, a method is provided for evaluating a fresh tissue sample during a medical procedure. The tissue sample is prepared during the medical procedure, such that the tissue will fluoresce under illumination. A plurality of spatial light patterns are projected onto a focal plane within the tissue sample. The fluorescence emitted from the sample is imaged as each of the plurality of spatial light patterns is projected on the tissue sample. The plurality of images are combined to provide a clinical image during the medical procedure.

DETAILED DESCRIPTION

The present invention discloses the development of a next-generation Rapid Optical Sectioning Specimen Scanner based on video-rate incoherent structured illumination microscopy and developed with consideration of the design requirements for rapid, high-area throughput fluorescence microscopy of intact surgical and biopsy specimens. An imaging system in accordance with an aspect of the present invention provides the ability to image fresh tissue immediately after removal from the subject to provide a clinically useful sample. By "fresh," it is meant that the tissue has been removed or exposed during a medical procedure occurring at a same time as the imaging of the sample. In other words, a fresh sample can be tissue removed from a patient during the procedure or tissue that is still within the patient, but made accessible as part of the medical procedure. It will be appreciated that a fresh sample will be significantly thicker than a traditionally prepared sample, increasing the challenge of the imaging process. By "clinically useful," it is meant that the image must have sufficient resolution to allow for meaningful clinical decision making associated with the medical procedure co-occurring with the imaging. For example, a well-known hallmark of cancer is increased cell nuclear density, due to the increased rate of growth in malignant tissue. To provide meaningful guidance to a surgeon looking for cancer margins on a freshly removed tissue sample, it is necessary that the image have sufficient resolution to reliably locate individual cell nuclei, which are on the order of ten micrometers in diameter.

To this end, a structured illumination approach is utilized with appropriate post-processing to provide a high-resolution, high-speed image of the fresh tissue sample. The disclosed method has sufficient lateral resolution and optical section thickness to effectively reduce out-of-focus fluorescence and isolate single nuclei, and a field of view which may be reasonably scaled to cover a large tumor resection margin, or other large surgical pathology specimen. The present invention employs a high-speed digital spatial light modulator and a complementary metal-oxide-semiconductor (CMOS) camera technology to achieve high resolution, optically-sectioned images of fluorescent samples at throughputs sufficient to allow for complete analysis of a sample during an ongoing medical procedure. Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner. To this end, wherever any of the phrases "for example," "such as," "including" and the like are used herein, the phrase "and without limitation" is understood to follow unless explicitly stated otherwise. Similarly "an example," "exemplary" and the like are understood to refer to a specific implementation detail of a more general inventive concept and are not intended to limit the claimed scope.

The term "substantially" allows for deviations from the descriptor that do not negatively impact the intended purpose. Therefore, for example, the phrase "wherein the lever extends vertically" means "wherein the lever extends substantially vertically" so long as a precise vertical arrangement is not necessary for the lever to perform its function. The terms "comprising" and "including" and "having" and "involving" (and similarly "comprises", "includes," "has," and "involves") and the like are used interchangeably and have the same meaning. Specifically, each of the terms is used as an open term meaning "at least the following," and does not exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

Figure 1:
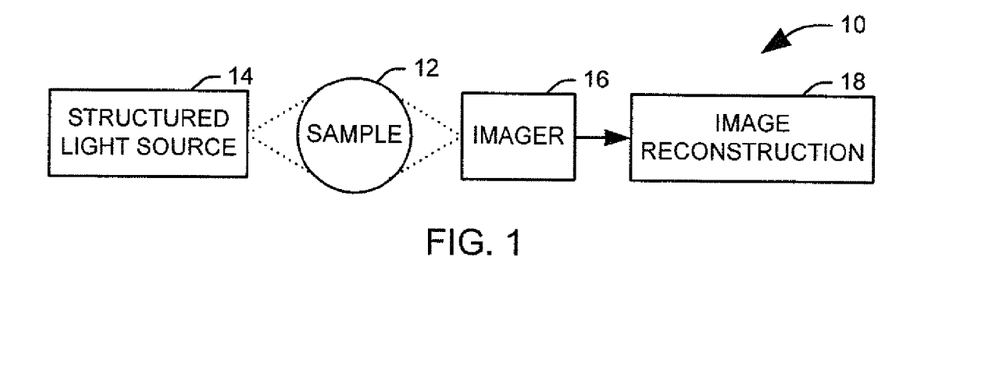
FIG. 1 illustrates a system for imaging a fresh tissue sample in accordance with an aspect of the present invention.

FIG. 1 illustrates a system 10 for imaging a fresh tissue sample 12 in accordance with an aspect of the present invention. It will be appreciated that the tissue sample 12 is prepared such that the sample will emit fluorescence when illuminated. In one implementation, the tissue sample 12 can be prepared in vivo using a non-toxic, tissue-enhancing fluorescent contrast agent for imaging in situ or upon removal of the tissue from the body. In another implementation, a fluorescent stain is applied to the tissue sample 12 after it has been removed from the body. For example, the fluorescent stain is selected from the group comprising acriflavine, acridine orange, alum-tetracycline, eosin, picric acid, DRAQ5™, and acid fuchsine. In another example, at least two stains are selected from the group as part of a multi-color, multi-stain process. The fluorescent stain may optionally be applied by at least one of spraying, dripping, dipping or pouring.

The system 10 includes a structured light source 14 configured to illuminate the tissue sample with a light beam having a specific pattern. In one implementation, the structured light source 14 can include a laser and a spatial light modulator, along with appropriate optical components to direct the beam of the laser onto or through the modulator and onto the sample and maintain desired spectral properties of the beam. In another implementation, the structured light source 14 can include a light emitting diode (LED) or other incoherent light source (e.g., a lamp) and one or more condensing lenses and appropriate optical components to project light onto or through a spatial light modulator and onto the tissue sample 12 and maintain desired spectral properties of the light. In one example, using coherent illumination, the spatial light modulator can be configured to modify the phase or the amplitude of the light source in order to project interference fringes onto the sample. In another example, using an incoherent light source, the light can be reflected from or passed through the spatial light modulator or to project an image of the spatial light modulator display onto the sample.

The fluorescence emitted from the illuminated tissue sample 12 is then imaged by an imaging system 16. It will be appreciated that, in addition to an imager, such as a camera, the imaging system 16 can include appropriate optical components for directing the fluorescence onto the imager and filtering out extraneous light. In one implementation, the structured light source 14 is configured to project the spatial light pattern in a specific plane within the tissue sample, with the imaging system 16 configured to have a focal plane coincident with the illuminated plane.

The image of the sample fluorescence can then be provided to a system control 18 to produce a human-comprehensible, clinically useful output for display to a user from the image. In one implementation, the system control 18 can instruct the structured light source 14 to project a series of spatial patterns onto the sample 12 and instruct the imaging system 16 capture at least one image associated with each of the series of spatial patterns. In another implementation, the system control 18 applies a high pass filter to the image to isolate cell nuclei and other features from the image. Alternatively or additionally, the system control 18 can include an automated image classification algorithm to categorize the tissue sample into one of a plurality of classes. For example, the classes can represent likelihoods that the tissue sample contains cancerous tissue, such that the system can identify abnormal cells and normal cells within the image.

The automated image classification algorithm can include, for example, one or more classification models, which can be combined via an appropriate arbitration scheme from their associated results and confidence values. These classification models can include artificial neural networks, regression models, support vector machines, ensemble learning models, and decision trees.

In other implementation, which can be used alone or in combination with the high pass filter and automated image classification algorithm described previously, a clinical image can then be generated as a synthesis of the images associated with the series of spatial patterns. In one example, the structured light source 14 can be instructed generate a first spatial pattern having an associated spatial frequency, a second spatial pattern having the same spatial frequency, but phase shifted from first spatial pattern by a first amount, for example, $2\pi/3$, and a third spatial pattern having the same spatial frequency, but phase shifted from first spatial pattern by a second amount, for example, $4\pi/3$. An image is captured for each of the spatial patterns and combined to provide a clinical image having an intensity value, $I_s$, for each pixel as a function of the intensity values, $I_1$, $I_2$, and $I_3$, for the corresponding pixel in the three images, such that:

$$I_s = \sqrt{(I_1-I_2)^2+(I_2-I_3)^2+(I_1-I_3)^2} \qquad \text{Eq. 1}$$

The illustrated imaging system 10 provides a number of advantages. For example, the speed of acquisition of SIM imaging is significantly increased. In one implementation, the system 10 can achieve 112.8 MHz pixel sampling rates, corresponding to a SIM framerate of 26.9 Hz, at 2048*2048 pixels per frame for SIM imaging using three raw images per SIM frame. The speed of acquisition is directly related to clinical potential. Since the goal is to cover large areas in a short amount of time at high resolution, the system 10 focuses on the pixel sampling rate. The inventor has achieved this both through judicious selection of components, such as ferroelectric SLM with microsecond switching times, and sCMOS camera with 100 Hz frame rates, as well as careful development of the control software 18 to optimize synchronization between the camera and the SLM pattern display.

Further, the system 10 includes a method for implementing autofocus at each position of the imaging system on the sample. Since the system 10 in configured to image fresh, intact specimens, the target is generally not flat. To enable contiguous imaging of the surface contours, the system control 18 provides an automated autofocus routine to bring the tissue surface into focus at each position in the mosaic. This allows for a consistent, high-resolution mosaic, as it is not practical for a human to manually focus the system thousands of times for imaging a single specimen.

Figure 2:
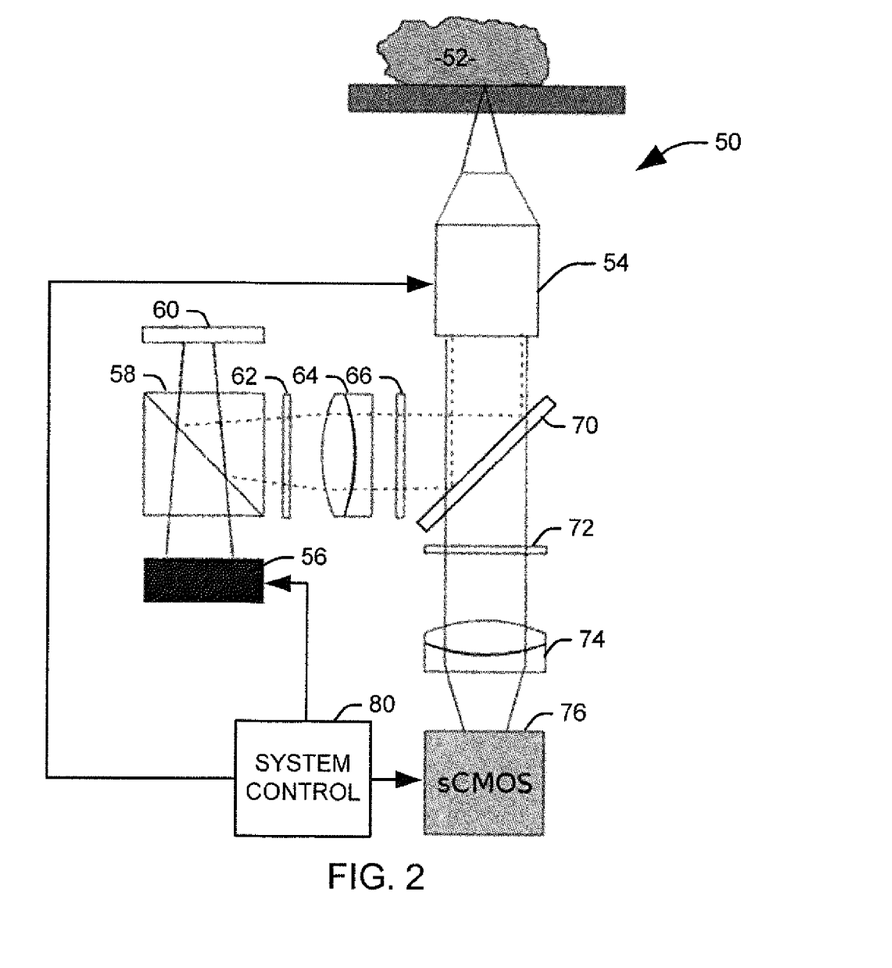
FIG. 2 illustrates a schematic of one example of a microscopy system for imaging a fresh sample in accordance with an aspect of the present invention.

FIG. 2 illustrates a schematic of one example of a microscopy system 50 for imaging a fresh sample 52 in accordance with an aspect of the present invention. The example system utilizes around a modular automated epi-fluorescence microscope platform, which incorporates a motorized XY stage and controller and a piezoelectric Z objective positioner used to reposition an objective lens assembly 54. Accordingly, the illustrated system 50 can provide images from samples having fields of view larger than a single frame by translating the microscope platform and creating a mosaic from the resulting images. In one implementation, this can be accomplished by translating the sample in the X and Y directions with serpentine or raster scanning in appropriate increments defined according to the size of camera sensor and the magnification provided by the objective lens assembly 54.

In the illustrated system, a light source 56 includes a blue light-emitting diode (LED) collected by an aspheric condenser lens. It will be appreciated, however, that the light could be provided in another manner, for example, via a laser and an associated beam expander. The collected light is then transmitted through a polarizing beam splitter (PBS) 58. The light is then provided to a spatial light modulator (SLM) 60. The spatial light modulator 60 can include, for example, a ferroelectric liquid crystal on silicon device, a digital micromirror device, a twisted nematic liquid crystal on silicon device, a mechanical grating device and a physical mask device. The spatial light modulator 60 can be operated in reflection mode or the spatial light modulator may be operated in transmission mode. The spatial light modulator 60 modulates one or both of the intensity and phase of the light source beam, such that the light output from the spatial light modulator has a defined spatial pattern.

In the illustrated implementation, the light is imaged onto a ferroelectric liquid-crystal-on-silicon spatial light modulator 60, which is placed in a plane conjugate to the sample plane. The LED output is imaged onto the spatial light modulator 60 to increase pattern contrast, increase illumination uniformity, and maximize étendue. In the illustrated implementation, the spatial light modulator 60 is configured such that light reflected from the spatial light modulator has a brightness, $s_i$, varying a dimension, x, in a sinusoidal pattern that can be represented as:

$$s_i(x,y) = 1 + m \cos(vx + \phi_i) \qquad \text{Eq. 2}$$

where m is a modulation depth, where varies between zero and one, v is a spatial frequency of the variation of the brightness, and $\phi_1$ is a phase shift for a given pattern. Each of the modulation depth and the spatial frequency are selected by the user to produce a pattern specific to a given application.

Once the excitation light has been modulated, it is passed through a clean-up polarizer 62 to improve contrast, a first tube lens 64, and a bandpass excitation filter 66. The filtered excitation light is reflected into the objective lens assembly 54 by a dichroic mirror 70 and forms an image of the spatial pattern associated with the spatial light modulator 60 onto the sample. The approximate power at the sample can be monitored, in some implementations, with a thermal power sensor placed above the objective lens assembly 54. Fluorescence from the sample is collected by the objective lens assembly 54, transmitted through the dichroic mirror 70, into a bandpass emission filter 72. The fluorescence is then imaged by a second tube lens 74 onto a scientific CMOS camera 76.

In one implementation of the illustrated system 50, synchronization and control of the light source 54, SLM 60, stage, objective, and camera was achieved 76 via custom software stored on a non-transitory computer medium at a system control 80. For example, sinusoidal grid patterns were generated at the software and uploaded to an on-board memory of the SLM 60 prior to imaging. The computation of the SIM image and assembly of the images into mosaics can be performed automatically during the acquisition procedure by custom software. A self-contained structured illumination module, containing the components comprising the optical path for the illumination 56, 58, 60, 62, 64, and 66 is mounted to the microscope platform, and the entire system fits comfortably on a custom a four foot wide and three foot deep wheeled lab bench.

In accordance with an aspect of the present invention, the system control 80 can synchronize the microscope platform, the light source 56, the SLM 60, and the CMOS camera 76. Specifically, a relative position of the objective lens assembly 54 and the sample 52 can be adjusted in precise increments defined by a field of view of the CMOS camera 76, and a mosaic image can be formed, representing the entire sample. The inventor has found that, through careful synchronization of these components 56, 60, and 76, it is possible to provide a mosaic image that is substantially free from artifact.

In one implementation, the SLM 60 can be operated in 8-bit bitplane weighting mode, and the pattern display was synchronized with the camera exposure by the system control 80. The ferroelectric liquid crystal displays of the SLM 60 operated in DC-balancing mode, in which each pixel is driven in positive and negative directions for equal durations. Therefore, to maintain contrast among the patterns, the light source 56 was triggered to only illuminate the SLM during the positive portion of the display cycle. At the maximum full-resolution camera frame-rate of about one hundred frames-per-second (fps) in internal trigger mode, the corresponding full-resolution SIM frame-rate was about 100/3=33 fps, as shown in Eq. 1, three sequential frames are used one SIM frame. This corresponded to about a 138.4 MHz pixel sampling rate for obtaining optically-sectioned images. The camera frame-rate, given by the reciprocal of the integration time for integration times greater than 10 ms, was adjusted to optimize the signal intensity from the sample. The duration of the 8-bit bitplane sequence used in one implementation was about 4.135 ms, and integration times that were integer multiples of the sequence duration, particularly at short integration times, were used to properly synchronize the pattern display with the camera integration times.

In one embodiment, the system 50 has a single-frame field-of-view (FOV) of about 1.3 mm×about 1.3 mm, at about 4.2 megapixel resolution, about 2048×2048 pixels. For the particular objective and camera used in one embodiment, the limiting factor for resolution is the camera pixel size, which is about 0.65 µm at the sample. The diffraction-limited optical resolution of the optical system is about 0.745 µm, using the commonly accepted formula of R=0.61$\lambda$/NA, where $\lambda$=about 550 nm for the emission bandpass filter used in this embodiment. Therefore, by the Nyquist criterion, the resolution of the system is limited not by diffraction, but by the size of the camera pixels, and is limited to 1.3 µm. Different FOV-to-optical-resolution ratios for various embodiments can be achieved by changing the imaging objective to lower or higher magnification models.

One implementation of the illustrated system 50 provides a relatively low cost and complexity solution to intraoperative specimen assessment. It is robust for routine clinical use, as there is no need for user adjustment and the only moving part is the microscope platform 52. The illustrated system 50 is compact and will fit on a custom wheeled lab instrument cart. Due to its light-efficient, wide-field imaging nature, it allows for quick evaluation and it is easily scalable for a wide range of resolution-to-coverage-area ratios simply by changing the microscope objective. The system relies on simple fluorescent analogs to standard histology dyes as contrast agents for highlighting histological features and do not rely on molecular recognition or have a need to set quantitative sensitivity thresholds, which is common with other molecular imaging applications. The system provides data in the form of histological images, which are well understood and accepted by the primary clinical practitioners, pathologists and surgeons. The ex vivo imaging paradigm is consistent with the current standard of care, is non-destructive, and does not require administering drugs or other agents to patients.

In providing an optimized multi-color, multi-stain fluorescence analog to standard histological staining applicable to fresh, unfixed tissues via spray or other administration method, the illustrated system 50 allows for high resolution of histological feature in a rapid-scanning system. This fluorescence histology approach could have implications for other applications beyond tumor margin assessment, such as in rapid screening of pathology specimens for directing sampling for permanent histopathology. These fluorescent analogs that can be applied to the excised tissue intraoperatively, through spraying, dipping, dripping, pouring or other application techniques, will allow the acquisition of images of histological detail previously only possible with labor intensive physical sectioning and staining techniques.

In one implementation, an optimized dye can be used to prepare the tissue sample. For example, cationic dye solutions, such as hematoxylin analogs, including acridine orange, acriflavine, proflavine, alum-tetracycline, and primuline can be adjusted from acidic to neutral pH, or anionic dye solutions, such as eosin or eosin analogs, may be adjusted from basic to neutral pH. The optimum formulation provides a balance between nuclear, cytoplasmic or stromal selectivity and staining intensity. It is likely that the fluorescence intensity will follow a parabolic behavior with concentration escalation, with maximum emission intensity when the tissue is dye-saturated, but not so concentrated that self-quenching or inner-filter effects reduce the fluorescence emission.

When using these optimized dyes, the system can include an additional camera for simultaneous dual-wavelength imaging. A dichroic splitter on the detection arm can be used to separate the emission bands of the two optimum fluorophores and direct them to cameras. If two distinct excitation wavelengths are in use, a dichroic combiner to combine two LEDs may be used with a multiband dichroic component to simultaneously illuminate the tissue. The inventor has found that a two-camera solution is current preferable to a single-camera arrangement, to facilitate high-speed imaging, although it will be appreciated that a single-camera arrangement could be used for dual-wavelength imaging with the use of appropriate filters.

Finally, in one implementation, the system control 80 can include a web-based streaming and zooming tool for remote viewing of large images. The tool can include multi resolution versions of the mosaic images, referred to as "image pyramids." This can be utilized for efficient viewing and diagnosis of the images, since it is not practical to use the full resolution raw images which can exceed twenty-five gigabytes in size.

The inventors have tested characterized the performance metrics of an example system using solid phantoms. To test the axial response of the system, a droplet of 1 μm fluorescent polystyrene beads was smeared onto the cover glass bottom of a culture dish, and covered with a layer of optically-clear polymer, such as poly(dimethylsiloxane) (PDMS). This is referred to herein as Phantom A. To simulate imaging of fluorescently-stained cell nuclei at the surface of tissue, 10 μm fluorescent beads were smeared onto the cover glass, and were covered with a layer of PDMS admixed with $TiO_2$ powder, to simulate the scattering of tissue (reduced scattering coefficient $\mu_s \sim 20$ $cm^{-1}$), referred to herein as Phantom B.

To ensure that the imaged sample is clinically useful, the inventors have determined how optimal parameters can be selected for the spatial light pattern used for structured illumination microscopy system of FIGS. 1 and 2. For example, the inventors have experimentally determined the effective optical section thickness of the SIM system. To this end, Phantom A was translated axially toward the objective and a sectioned image was acquired using structured illumination at each 10 μm step. The mean fluorescence intensity from a region of interest (ROI) within the sectioned image was plotted against axial depth to determine the section thickness of the system.

Figure 3:
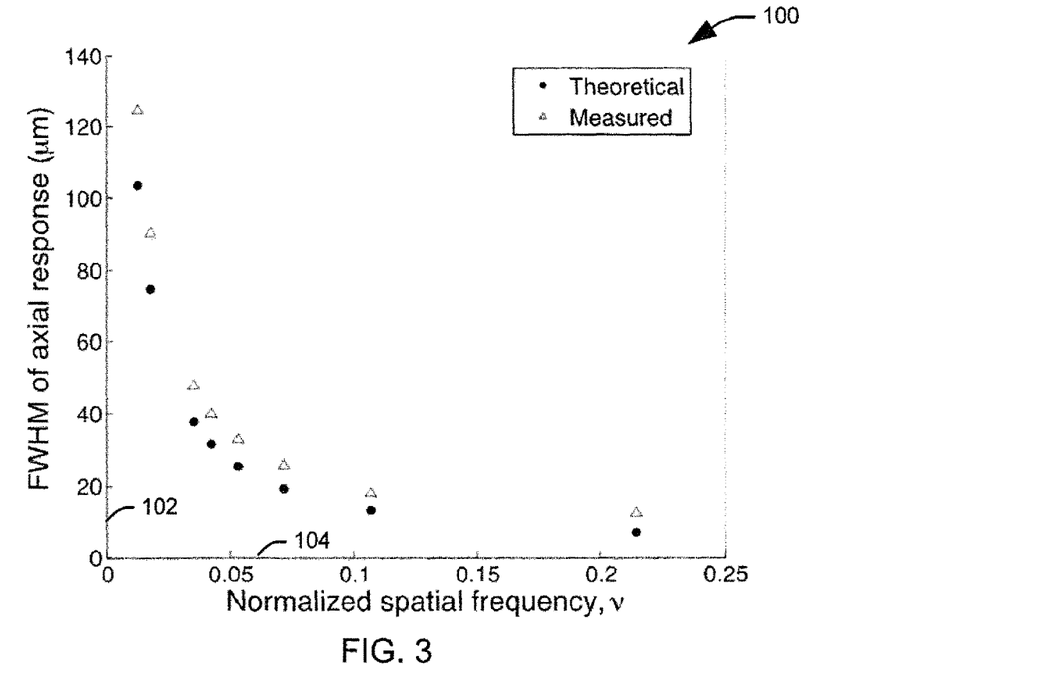
FIG. 3 illustrates a plot of the measured and theoretical full width at half maximum (FWHM) of the axial response of the system of FIG. 2 as a function of normalized spatial frequency on a prepared phantom.

FIG. 3 illustrates a plot 100 of the measured and theoretical full width at half maximum (FWHM) of the axial response of the system of FIG. 2 as a function of normalized spatial frequency, which was measured using Phantom A. The vertical axis, 102, represents the FWHM, and the horizontal axis 104 represents the normalized spatial frequency, $$\tilde{v} = \frac{v\lambda}{n\sin(\alpha)}.$$

For each pattern frequency, the microscope objective was scanned through the sample in about 1-3 μm increments, depending on the frequency, and a structured illumination microscopy image was acquired at each z-plane. The axial response of the system was determined by averaging the intensity of a region-of-interest (ROI) containing the smear of subdiffraction polystyrene beads, and plotting the mean intensity versus z-position.

As can be seen from the chart, the optical section thickness decreases as the grid pattern spatial frequency is increased, and there is fairly good agreement between the measured and theoretical axial responses. The inventor has determined that there is little benefit to using normalized spatial frequencies larger than about 0.17, since the increase in optical sectioning power is small and may be outweighed by decreasing SNR. For incoherent SIM, the optimum normalized spatial frequency is lower, at around 0.1, beyond which there is little decrease in optical section thickness. This is an advantage of incoherent SIM, in that the optical section thickness for a given normalized spatial frequency is smaller than that for coherent SIM, and allows lower pattern frequencies with higher SNR to be used to obtain the same optical sectioning effect.

In addition, the section thickness was measured over a range of illumination pattern frequencies, for each of a range of phantoms with different scattering properties. The Stokseth approximation, given below as Eq. 3, was found to provide a valid theoretical optical section thickness value.

$$I(u) = 2f(\tilde{v}) \frac{J_1\left[2u\tilde{v}\left(1 - \frac{\tilde{v}}{2}\right)\right]}{2u\tilde{v}\left(1 - \frac{\tilde{v}}{2}\right)} \quad \text{Eq. 3}$$

where $$f(\tilde{v}) = 1 - 0.69\tilde{v} + 0.0076\tilde{v}^2 + 0.043\tilde{v}^3, \tilde{v} = \frac{v\lambda}{n\sin(\alpha)},$$

$$u = \frac{8\pi zn}{\lambda}\sin\left(\frac{\alpha}{2}\right),$$

I(u) is the optical sectioning axial response, $J_1$ is the Bessel function of the first kind, v is the grid frequency, $\tilde{v}$ is the normalized grid frequency, λ is the emission wavelength, n sin(α) is the NA of the objective, z is the real axial distance, and u is the normalized axial distance.

The inventor then determined a relationship between section thickness and illumination frequency to assist in selecting the appropriate frequency for imaging. The modulation depth, m, as previously shown Eq. 2, is a quantity which represents the amplitude of the sinusoidal illumination pattern transferred onto the sample. The intensity of the received fluorescence in the sectioned image, $I_s$, can be described as a function of the in-focus fluorescence, f(x,y) and the modulation depth as:

$$I_s = \frac{3m}{2\sqrt{2}} f(x, y) \quad \text{Eq. 4}$$

It can be seen that the resulting signal of the sectioned image, $I_S$, is described primarily by the in-focus fluorescence, f(x,y). However, a coefficient dependent on modulation depth, m, appears in this equation and scales f(x,y) accordingly. In addition, modulation depth decreases with spatial frequency because of the natural decay in the shape of the incoherent optical transfer function of the objective. The modulation depth can be measured on a pixel-by-pixel basis using three phase shifted images, $I_1$, $I_2$, and $I_3$ as described in Eq. 1, as follows:

$$m(x, y) = \sqrt{\frac{8}{3}\left[\left(\mu_1 - \frac{1}{2}\right)^2 + \left(\mu_2 - \frac{1}{2}\right)^2 + \left(\mu_3 - \frac{1}{2}\right)^2\right]} \quad \text{Eq. 5}$$

where $$\mu_i = \frac{3I_i}{2(I_1 + I_2 + I_3)}.$$

The modulation depth, m(x,y) at each pixel within a given image can be measured, and a median value chosen to represent the modulation depth over a specific region of interest in each image. This median modulation depth was measured for a range of frequencies using the same region of interest and sample location on the same fluorescent phantoms used to characterize the optical section thickness. The phantom was simply placed in focus at the sample plane and three phase shifted images at multiple illumination frequencies were acquired. The inventor has found that, because of the direct relationship of modulation depth on recovered signal and the inverse relationship between signal-to-noise ratio and modulation depth, an illumination frequency yielding both a sufficient modulation depth and optical section thickness is selected to generate a clinically useful result. The signal-to-noise ratio of a sectioned image is a quantitative measurement of image quality, which is directly influenced by modulation depth as follows:

$$SNR_{Uniform} = \frac{\langle I_W \rangle}{\delta(I_W)} \qquad \text{Eq. 6}$$

$$SNR_{Sectioned} = \frac{mI_S\sqrt{3}}{2\delta(I_W)} \qquad \text{Eq. 7}$$

where $I_W=2(I_1+I_2+I_3)/3$.

$I_W$ represents the traditional wide-field image that is reconstructed from the three phase shifted structured illumination images. The sectioned image, $I_S$, is calculated using Eq. 1. The modulation depth has a direct impact on the SNR of the sectioned image, as shown in Eq. 7. The inventor has characterized measurements of optical section thickness, modulation depth and corresponding SNR at multiple frequencies to provide insight into selecting a single illumination frequency that provided the best balance among these parameters.

Images were taken on the phantoms consisting of single layer of 10-μm diameter fluorescence spheres. The spheres were embedded in PDMS and $TiO_2$ giving the surrounding medium a biologically relevant reduced scattering coefficient value ($\mu_s=10$ cm$^{-1}$) to introduce background fluorescence. Each image was normalized by dividing each pixel by the maximum intensity within the image. The images clearly demonstrate the improvement seen in structured illumination compared to uniform illumination. The specific illumination frequency chosen to acquire these images was 31.7 μm. The contrast ratio was calculated directly in both images, which showed a significant quantitative improvement, 830% greater in the sectioned image over the uniform image.

The optical sectioning strength for each of a plurality of illumination frequencies was measured using the three phantoms, having scattering coefficients, in cm$^{-1}$, of 0, 10, and 20, and the methods described previously. Specifically, for the 4× objective, the absolute illumination frequencies at the sample plane, in mm$^{-1}$, included 101, 67, 50.3, 47.7, 40.7, 31.7, 24.1, and 19.6. For the 2× objective, the frequencies included 25.1, 16.7, 12.5, and 10.2. The numerical aperture of both lenses was 0.1. It was determined that optical sectioning thickness decreased as the illumination spatial frequency increased in a non-linear relationship. Statistical analysis of the data using a Student's t-test demonstrated no significant difference between scattering levels. The measured optical section thickness data was compared to a theoretical value acquired using the Stokseth approximation to the optical transfer function as shown in Eq. 3. The measured data of the single axial scan matched well with the Stokseth approximation using the variables v=19.6 mm$^{-1}$, 2=520 nm, and NA=0.1. The measured optical section thicknesses showed excellent agreement with the theoretical optical section thickness calculated using the Stokseth approximation.

After determining the frequency dependence of optical section thickness, the inventor measured the modulation depth at each illumination frequency. The measured modulation depths in two separate phantoms ($\mu_s=0$ and 10 cm$^{-1}$) for each frequency were calculated as the median value over an identical ROI in each image for all illumination frequencies using the same laser illumination power and charge coupled device integration time. Error bars were generated by computing the standard deviation of modulation depth over ten images at the same sample location. The data clearly indicated an inverse relationship between modulation depth and illumination frequency. In addition, a significant decrease in modulation depth at all frequencies was seen in the phantom with a scattering coefficient of 10 cm$^{-1}$ compared to the non-scattering phantom.

Figure 4:
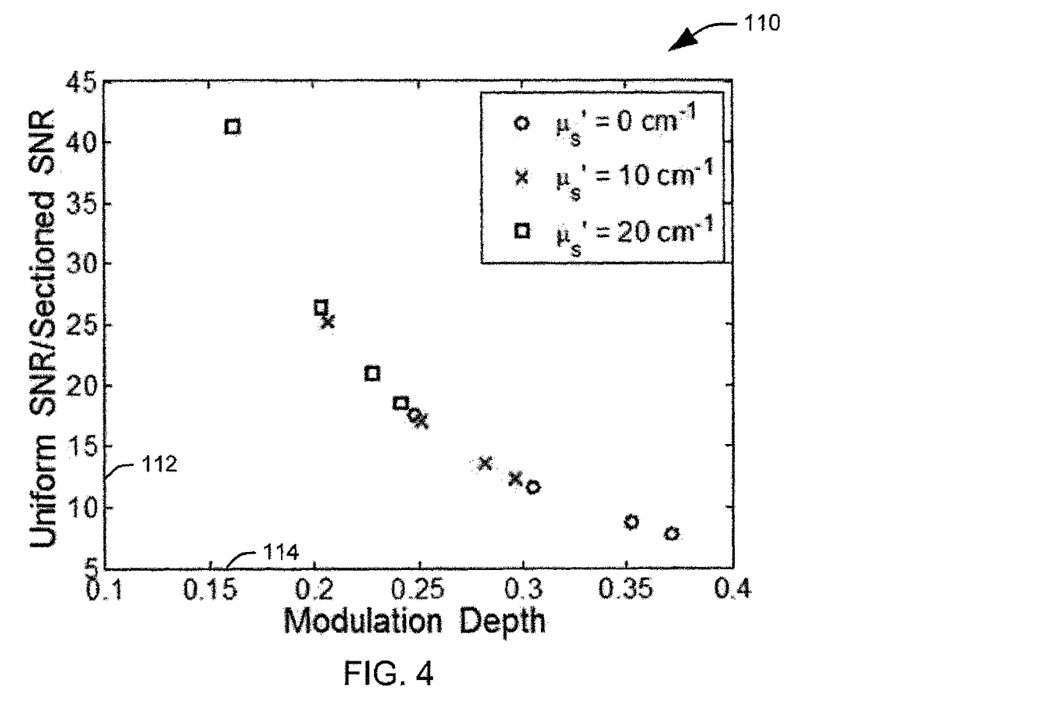
FIG. 4 illustrates a plot of the ratio of uniform signal-to-noise ratio (SNR) to sectioned SNR against modulation depth.

FIG. 4 illustrates a plot 110 of the ratio of uniform signal-to-noise ratio (SNR) to sectioned SNR against modulation depth. This ratio, represented by the vertical axis 112, demonstrates the reduction in SNR of structured illumination microscopy compared to standard wide-field microscopy. A horizontal axis 114 of the plot 100 represents modulation depth. As can be seen from the plot 100, the ratio decreases with modulation depth, indicating less degradation in SNR at higher modulation depths compared to lower modulation depths.

The imaging speed of the system and resulting signal-to-background ratio (SBR) was measured using Phantom B. A single region of the phantom was imaged in SIM mode using about 12.4 ms, about 25 ms, about 50 ms, and about 100 ms integration times, corresponding to about 26.9, about 13.3, about 6.7, and about 3.3 Hz SIM imaging rates, respectively. Corresponding non-SIM images were collected for comparison. Ten sequential images were acquired for each integration time. The SBR for a single image was measured by averaging the intensity of a bead-containing image region of interest (ROI), and dividing by the average intensity of an identically-sized ROI without any beads. The average and standard deviation of the SBR was calculated over the ten sequential images using the same ROIs. The LED output was adjusted to obtain the highest available signal without saturating the scientific CMOS detector prior to imaging. In addition, mosaics of the phantom were obtained.

Figure 5:
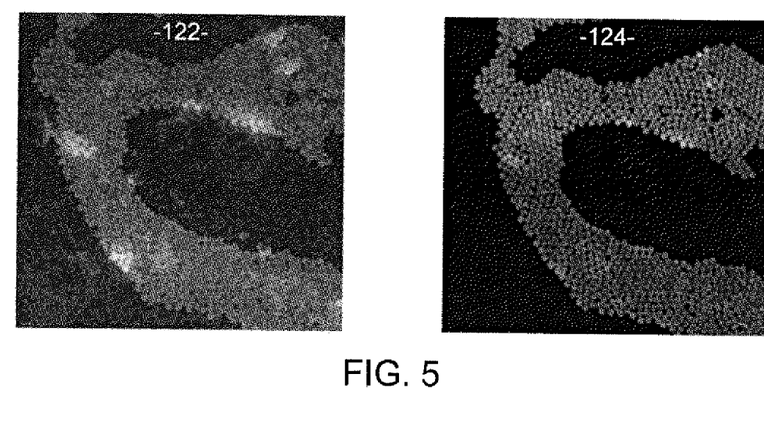
FIG. 5 illustrates two images of prepared phantom imaged with and without the use of structure illumination microscopy (SIM)
Figure 6:
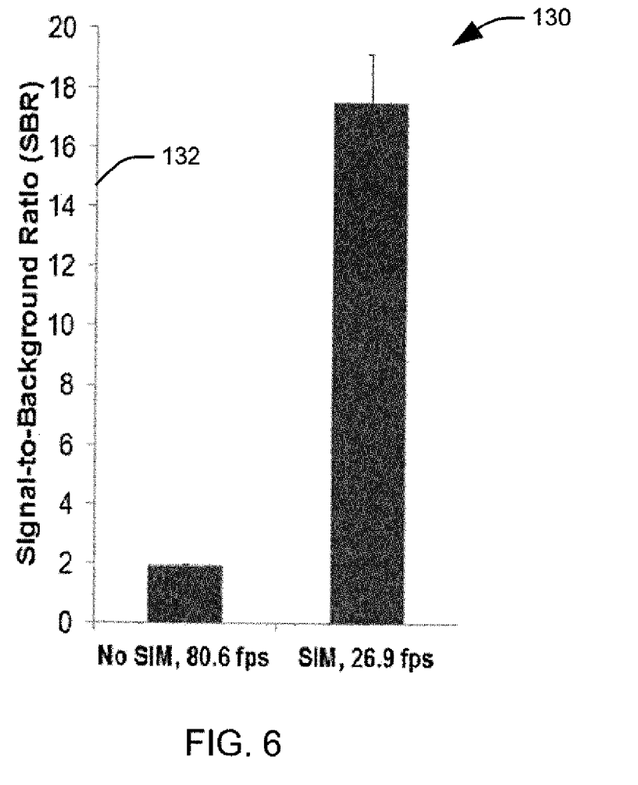
FIG. 6 is a bar chart demonstrating an increase in SBR in the SIM image of FIG. 5 over the other image using a comparable frame rate.

The signal-to-background ratio (SBR) as a function of imaging speed was calculated from the series of phantom images. A normalized pattern spatial frequency of about 0.05 was used for SIM in these images from one embodiment. FIG. 5 illustrates two images 122 and 124 of Phantom B. In the first image 122, the phantom is imaged at 80.6 frames per second (fps) without using SIM. In the second image 124, the phantom was imaged at 26.9 effective fps, with each frame being formed from three constituent images representing different spatial patterns, as described above with respect to Eq. 1. It will be appreciated that the SIM image 124 provides a significant increase in contrast and resolution. FIG. 6 is a bar chart 130 demonstrating the increase in SBR, represented by the vertical axis 132, in the SIM images using a comparable frame rate. It will be appreciated that the SBR for the SIM image 124 is significantly higher than the SBR for the non-SIM image 122, demonstrating the improvement in contrast due to optical sectioning due to SIM.

Figure 7:
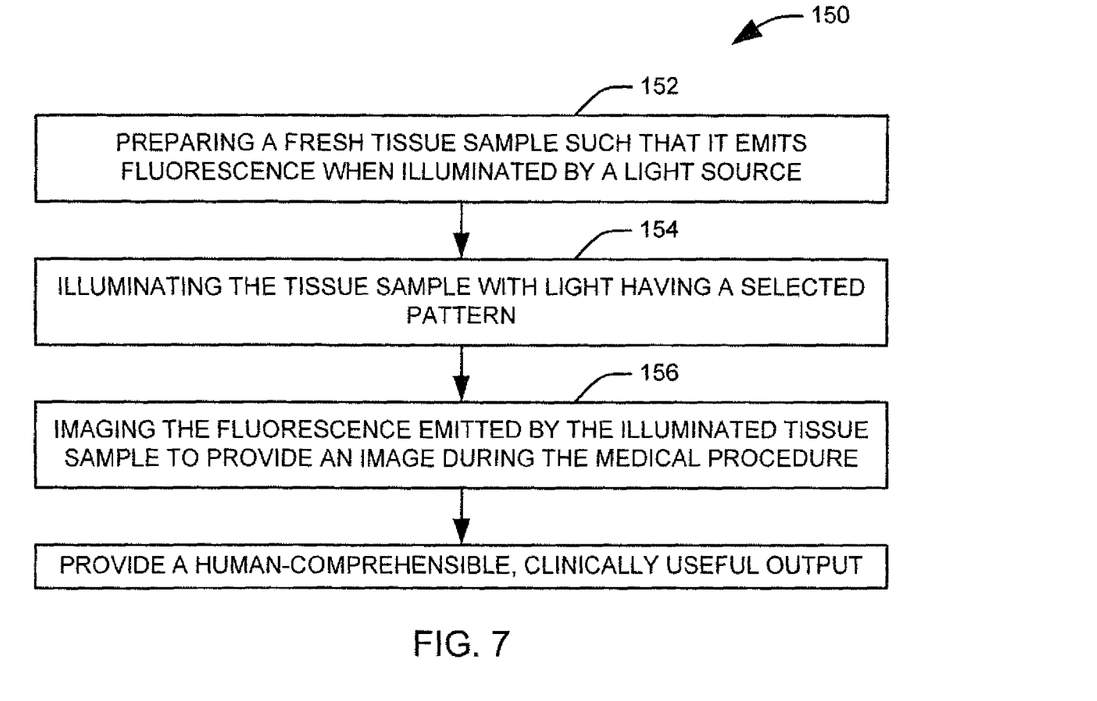
FIG. 7 illustrates a method for rapidly evaluating a tissue sample removed during a medical procedure.

In view of the foregoing structural and functional features described above in FIGS. 1-6, example methodologies will be better appreciated with reference to FIG. 7. While, for purposes of simplicity of explanation, the methodology of FIG. 7 is shown and described as executing serially, it is to be understood and appreciated that the present invention is not limited by the illustrated order, as some actions could in other examples occur in different orders and/or concurrently from that shown and described herein.

FIG. 7 illustrates a method 150 for rapidly evaluating a tissue sample removed during a medical procedure. At 152, the tissue sample is prepared such that the tissue will fluoresce under illumination. In one implementation, preparing the tissue sample includes applying a fluorescent stain to the tissue sample removed from a patient. The fluorescent stain can be selected from the group comprising acriflavine, acridine orange, alum-tetracycline, eosin, DRAQ5™, picric acid, and acid fuchsine, for example, via spraying, dripping, dipping, or pouring. In another implementation, preparing the tissue sample includes a administering a non-toxic, tissue-enhancing fluorescent contrast agent to the patient and imaging the tissue either after removal or in situ. In yet another application, applying the fluorescent stain to the tissue sample comprises applying at least two stains selected from the group above as part of a multi-color, multi-stain process. At 154, spatially patterned illumination is projected onto the tissue sample. In one implementation, projecting spatially patterned illumination onto the tissue sample includes producing light at one of a laser and a light emitting diode and reflecting the produced light from a spatial light modulator assembly.

At 156, the fluorescence emitted from the sample is imaged during the medical procedure. In one implementation, each of a first spatial pattern, having a spatial frequency, and a plurality of other spatial patterns, having the spatial frequency and an associated phase shift relative to the first pattern, are projected onto the tissue sample in a predetermined sequence. The fluorescence emitted from the sample is imaged during each spatial illumination pattern to produce a plurality of images. In one implementation, each image of the plurality of images can themselves represent composites, or mosaics, of a plurality of individual images representing different portions of the tissue sample. For example, to capture one of the plurality of images, the sample and at least a portion of an imaging system, such as the objective lens, can be placed in a first relative position, and a first component image can be captured, representing the fluorescence emitted from a first location on the sample. By moving either the sample or the portion of the system, the sample and the imaging system can be placed in a second relative position. A second component image can be captured, representing the fluorescence emitted from a second location on the tissue sample. This can be repeated until all portions of the sample are adequately represented. The various component images can then be combined to provide one of the plurality of images.

At 158, a human-comprehensible, clinically useful output is provided. In one implementation, this output is a synthesis of several optically sectioned images, taken at different phase shifts as described in 156, to produce a clinical image. For example, the phase shift of the spatial illumination pattern for an $i^{th}$ image in a series of n images can be equal to $2\pi(i-1)/n$. The resulting images can then be combined such that combining the images such that an intensity for a given pixel of the clinical image, $I_s$, can be represented by a combination of corresponding pixels, I, such that:

$$I_s = \sqrt{\sum_{i=1}^{n-1} \sum_{j=i+1}^{n} (I_i - I_j)^2}$$ Eq. 8

In another implementation, the clinically-useful output is provided when an optically sectioned image or a clinical image formed from multiple images has a high pass filter applied to it to isolate and clarify small structures, such as cell nuclei, within the image. In yet another implementation, one of the optically sectioned image and the clinical image can be provided to an automated image classification algorithm to classify all or a portion of the tissue. For example, the classification algorithm can locate regions of healthy and diseased tissue within the sample according to one or more classification features, such as the density of cell nuclei.

Figure 8:
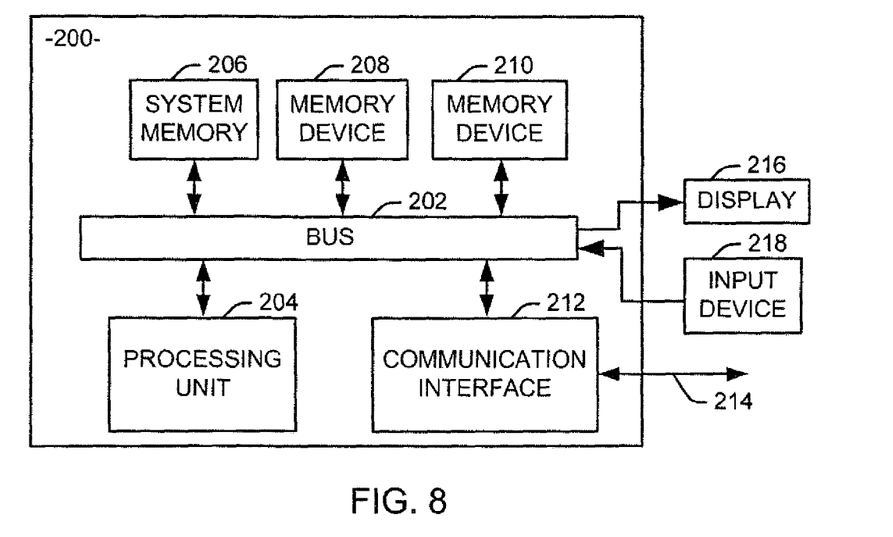
FIG. 8 is a schematic block diagram illustrating an exemplary system of hardware components capable of implementing examples of the systems and methods disclosed in FIGS. 1-7.

FIG. 8 is a schematic block diagram illustrating an exemplary system 200 of hardware components capable of implementing examples of the systems and methods disclosed in FIGS. 1-7, such as the structured illumination microscopy system illustrated in FIGS. 1 and 2. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an imaging system in accordance with the present invention, such as the system control 18. Computer executable logic for implementing portions of the imaging system reside on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium or media that participates in providing instructions to the processing unit 204 for execution. It will thus be appreciated a computer readable medium is non-transitory and can include multiple discrete media that are operatively connected to the processing unit, for example, via one or more of a local bus or an network connection.

What have been described above are examples of the present invention. It is, of course, not possible to describe every conceivable combination of components or methodologies for purposes of describing the present invention, but one of ordinary skill in the art will recognize that many further combinations and permutations of the present invention are possible. While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. Accordingly, the present invention is intended to embrace all such alterations, modifications, and variations that fall within the scope of the appended claims. No feature of the invention is critical or essential unless it is expressly stated as being "critical" or "essential."

What is claimed is:

1. A method comprising:
   projecting light through a spatial light modulator in a plurality of orientations to provide a plurality of spatial light patterns sequentially illuminating a focal plane within an excised tissue sample, wherein the tissue sample is pre-stained with a fluorescent contrast agent;
   imaging the fluorescence emitted from the sample as each of the plurality of spatial light patterns are projected on the tissue sample to form a plurality of microscopy images; and
   combining the plurality of microscopy images to form an image of an optical section of the excised tissue sample, wherein the image exhibits an improved contrast due to rejecting out of focus light in the plurality of microscopy images during the combining.

2. The method of claim 1, further comprising preparing the excised tissue sample such that the tissue will fluoresce under illumination, wherein preparing the excised tissue sample comprises applying a solution of the fluorescent contrast agent to the excised tissue sample.

3. The method of claim 1, wherein the fluorescent contrast agent comprises at least one of an anionic dye solution or a cationic dye solution.

4. The method of claim 1, wherein the fluorescent contrast agent comprises an anthraquinone dye, Eosin, or Acridine orange.

5. The method of claim 1, wherein the fluorescent contrast agent comprises Acriflavine, Proflavine, Acid fuchsine, Methylene blue, Picric acid, Cresyl violet, Tetracycline, Alum tetracycline, Fluorescein, Aniline blue Fast green, boron-dipyrromethene, Rhodamine, Sulforhodamine, 4',6-diamidino-2-phenylindole, Propidium iodide, or Alcian blue.

6. The method of claim 1, wherein the light is produced by a laser and/or a light emitting diode.

7. A system comprising:
   a light source to project a light beam onto an excised tissue sample;
   a spatial light modulator to modulate the light beam, wherein the spatial light modulator is arranged in a plurality of orientations to form a plurality of illumination patterns onto a focal plane of the excised tissue sample; and
   an imaging system to produce a plurality of microscopy images from fluorescence emitted from the tissue sample due to a plurality of illumination patterns, wherein the plurality of microscopy images are combined to provide an image of an optical section of the excised tissue sample with an improved contrast, wherein the improved contrast is provided by rejecting out of focus light in the plurality of microscopy images.

8. The system of claim 7, wherein the light source comprises:
   a light emitting diode; and
   a condensing lens positioned to collect light from the light emitting diode and provide the collected light to the spatial light modulator.

9. The system of claim 7, wherein the light source comprises:
   a laser; and
   a beam expander positioned in an optical path of a beam from the laser.

10. The system of claim 7, wherein the spatial light modulator comprises: ferroelectric liquid crystal on silicon device, a digital micromirror device, a twisted nematic liquid crystal on silicon device, a mechanical grating device or a physical mask device.

11. The system of claim 7, wherein the excised tissue sample is stained with a fluorescent contrast agent.

12. The system of claim 11, wherein the fluorescent contrast agent comprises an anionic dye solution or a cationic dye solution.

13. The system of claim 11, wherein the fluorescent contrast agent comprises an anthraquinone dye.

14. The system of claim 11, wherein the fluorescent contrast agent comprises Eosin, or Acridine orange.

15. The system of claim 11, wherein the fluorescent contrast agent comprises Acriflavine, Proflavine, Acid fuchsine, Methylene blue, Picric acid, Cresyl violet, Tetracycline, Alum tetracycline, Fluorescein, Aniline blue Fast green, boron-dipyrromethene, Rhodamine, Sulforhodamine, 4',6-diamidino-2-phenylindole, Propidium iodide, or Alcian blue.

* * * * *